United States Patent [19]

Shewmaker et al.

[11] Patent Number: 5,759,829
[45] Date of Patent: *Jun. 2, 1998

[54] ANTISENSE REGULATION OF GENE EXPRESSION IN PLANT CELLS

[75] Inventors: Christine K. Shewmaker, Woodland; Jean C. Kridl; William R. Hiatt, both of Davis; Vic Knauf, Winters, all of Calif.

[73] Assignee: Calgene, Inc., Davis, Calif.

[*] Notice: The term of this patent shall not extend beyond the expiration date of Pat. No. 5,107,065.

[21] Appl. No.: 463,213

[22] Filed: Jun. 5, 1995

Related U.S. Application Data

[63] Continuation of Ser. No. 750,505, Aug. 27, 1991, Pat. No. 5,453,566, which is a continuation-in-part of Ser. No. 240,408, Aug. 30, 1988, Pat. No. 5,107,065, which is a continuation of Ser. No. 920,574, Oct. 17, 1986, abandoned, which is a continuation of Ser. No. 845,676, Mar. 28, 1986, abandoned.

[51] Int. Cl.$^6$ ............ C12N 15/84; C12N 15/29; A01H 5/00; A01H 1/02
[52] U.S. Cl. ............ 435/172.3; 435/419; 536/23.6; 536/24.1; 536/24.5; 47/58; 47/DIG. 1; 800/205
[58] Field of Search ............ 435/172.3, 240.4, 435/419; 536/23.6, 24.1, 24.5; 800/205; 47/58, DIG. 1

[56] References Cited

U.S. PATENT DOCUMENTS

| | | | |
|---|---|---|---|
| 4,740,463 | 4/1988 | Weinberg et al. | 435/172.3 |
| 4,801,540 | 1/1989 | Hiatt et al. | 435/172.3 |
| 5,023,243 | 6/1991 | Tullis | 514/44 |
| 5,107,065 | 4/1992 | Shewmaker et al. | 800/205 |
| 5,190,931 | 3/1993 | Inouye et al. | 435/91 |
| 5,208,149 | 5/1993 | Inouye et al. | 435/91 |
| 5,272,065 | 12/1993 | Inouye et al. | 435/91.1 |
| 5,453,566 | 9/1995 | Shewmaker et al. | 800/205 |

FOREIGN PATENT DOCUMENTS

| | | |
|---|---|---|
| 0 159 779 | 2/1985 | European Pat. Off. |
| 0 140 308 | 5/1985 | European Pat. Off. |
| 0 223 399 | 10/1986 | European Pat. Off. |
| 0 223 452 | 10/1986 | European Pat. Off. |
| 0 240 332 | 1/1987 | European Pat. Off. |
| 0 271 988 | 11/1987 | European Pat. Off. |
| 0092574 | 4/1992 | European Pat. Off. |
| 86/05516 | 9/1986 | WIPO |
| 88/01645 | 3/1988 | WIPO |

OTHER PUBLICATIONS

Green, et al., "The Role of Antisense RNA in Gene Regulation" Ann.Rev. Biochem 1986 55:569–97.
Grierson, et al., *Tomato Biotechnology* pp.309–323 (1987) Alan R. Liss, Pub.
Grierson, et al., *Phil. Trans. R. Soc. Lond.* B. 314:399–410 (1986).
Grierson et al., *Planta* 163:263–271 (1986).
Kramer, et al., *Horticultural Biotechnology* pp.347–355 (1990) Wiley-Liss, Inc.
Kramer, et al., *Trends in Biotechnology* 7:191–194 (1988).
Rosenberg, et al., *Nature* (1985) 313:703–706.
Kim et al., *Cell* (12985) 42:129–138.
Izant and Weintraub, *Science* (1985) 229:345–352.
Melton, *PN S USA* (1985) 82:144–148.
Coleman, et al., *Nature* (1985) 315: 601–603.
Rubenstein et al., *C.R. Acad. Sc.* Paris (1984).
Ecker and Davis, *Proc. Natl. Acad. Sci. USA* (1986) 83:5372–5376.
DellaPenna et al., *Proc. Natl. Acad. Sci. USA* (1986) 83:6420–6424.
Grierson et al., *Nucleic Acids Research* (1986) 14:8595–8603.
Crowley et al., *Cell* (1985) 43:63–641.
Mansson et al., *Chemical Abstracts* (1985) 103:211, No. 1555198q.
Hobson et al., *Chemical Abstracts* (1985) 101:416, No. 127096v.
Helmer et al., *Biotechnology* (Jun. 1984) :520–527.
Loesch-Fries et al., *Journal of Cellular Biochemistry* (1986) vol. 0, No. 10, Part C, p. 41 Abstract No. J108.
Slater, et al., *Plant Molecular Biology* (1985) 5:137–147.
Pressey et al., *Chemical Abstracts* (1982) 97:456, No. 88858x.
Delauney, et al., *Proc. Natl. Acad. Sci. USA* (1988) 85:4300–4304.
Sandler et al., *Plant Molecular Biology* (1988) 11:301–310.
Sheehy, et al., *Proc. Natl. Acad. Sci. USA* (1988) 85:8805–8809.
Rothstein et al., *Proc. Natl. Acad. Sci. USA* (1987) 84:8439–8443.
Smith et al., *Nature* (1988) 334:724–726.
Preiss et al., *Nature* (1985) 313:27–32.
Izant et al., *Cell* (1984) 36:1007–1015.
Andrew Travers, *Nature* (1964) 311:410.
Weintraub, et al., *TIG* (1985) 1:22–25.
McGarry et al., *Proc. Natl. Acad. Sci. USA* (1986) 83:399–403.
Pestka et al., *Proc. Natl. Acad. Sci. USA* (1984) 81:7525–7528.
Mizuno et al., *Proc. Natl. Acad. Sci. USA* (1984) 81:1966–1970.

*Primary Examiner*—David T. Fox

[57] ABSTRACT

Regulation of expression of genes encoded for in plant cell genomes is achieved by integration of a gene under the transcriptional control of a promoter which is functional in the host and in which the transcribed strand of DNA is complementary to the strand of DNA that is transcribed from the endogenous gene(s) one wishes to regulate. The integrated gene, referred to as antisense, provides an RNA sequence capable of binding to naturally existing RNAs, exemplified by polygalacturonase, and inhibiting their expression, where the anti-sense sequence may bind to the coding, non-coding, or both, portions of the RNA. The antisense construction may be introduced into the plant cells in a variety of ways and be integrated into the plant genome for inducible or constitutive transcription of the antisense sequence. A wide variety of plant cell properties may be modified by employing this technique.

17 Claims, 5 Drawing Sheets

```
       StyI
       SecI
       NcoI
    EcoRI  NlaIII                       DdeI                         DdeI                      NdeI
       |  DsaI  |                    RsaI  AluI                      AluI                      HphI
       |   |    |                      |    |                          |                         |
 1  GAATTCCATGGGATTAAAGTGATTAATGTACTTAGCTTTGGAGCTAAGGGTGATGGAAAAACATATGAT   69
            GlyIleLysValIleAsnValLeuSerPheGlyAlaLysGlyAspGlyLysThrTyrAsp
        2       7                    30   32    36            44 45        62    64
                7
                7
                7

XbaI
                                         Nsp(7524)I
                        NlaIII      TthlllI  MaeI                         NlaIV
     SspI                  |           |   |                                |
       |                   |           |   |                                |
70  AATATTGCATTTGAGCAAGCATGGAATGAAGCATGTTCATCTAGAACACCTGTTCAATTGTGGTTCCT  138
     AsnIleAlaPheGluGlnAlaTrpAsnGluAlaCysSerSerArgThrProValGlnPheValValPro
      73               93            102  105   111                  135
                                          105
                                               110

FIGURE 1A
```

```
                                                              XhoII
                                                              NlaIII
                                                    MboI
                                          TthlllII  MboI    DpnI
                                          AvaII     BglII
                    HphI      HgiEII      AsuI
         MboII
139 AAAAACAAGAATTATCTTCTCAAGCAAATCACCTTTTCAGGTCCATGCAGATCTTCTATTTCAGTAAAG 207
    LysAsnLysAsnTyrLeuLeuLysGlnIleThrPheSerGlyProCysArgSerIleSerValLys
    146              160          169       176  179    183  186  188
                                                 179         188
                                                                  188
                                                                  190

XhoII
    NlaIV
    DpnI
    MboI
    BinI BamHI
208 ATTTTTGGATCC 219
    IlePheGlySer
    210  215
         215
         217
         217
         215
```

FIGURE 1B

ANTISENSE REGULATION OF GENE EXPRESSION IN PLANT CELLS

CROSS-REFERENCE TO RELATED APPLICATIONS

This application is a continuation of U.S. application Ser. No. 07/750,505, filed Aug. 27, 1991, now U.S. Pat. No. 5,453,566, which is a continuation-in-part of U.S. application Ser. No. 07/240,408, filed Aug. 30, 1988, which issued as U.S. Pat. No. 5,107,065 on Apr. 21, 1992, which is a continuation of U.S. application Ser. No. 06/920,574, filed Oct. 17, 1986, now abandoned, which is a continuation of U.S. application Ser. No. 06/845,676, filed Mar. 28, 1986, now abandoned, which disclosures are incorporated herein by reference.

BACKGROUND OF THE INVENTION

The modification of plants by genetic engineering has lagged behind the understanding and utilization of the molecular biology of unicellular organisms and mammalian cells. Techniques that have proven effective for stable transformation of unicellular microorganisms or mammalian cells with foreign DNA have not found useful analogy with plant cells. Therefore, despite the many achievements involved with unicellular microorganisms and mammalian cells, the number of achievements with plant cells has been substantially fewer and the experience with the other types of organisms has not been readily translatable into successful practices with plant cells.

In many situations it will be desirable to modify an existing trait of a plant cell, rather than introduce a new trait. Thus, one may wish to modify the activity of a particular enzyme, provide for the preferential expression of one allele as compared to another, one isozyme as compared to another, or the like. In many instances one may only wish to reduce the amount of expression of a structural gene, rather than inhibit expression entirely. It is therefore of interest to develop techniques which will allow for directed modification of the phenotype of particular plant cells, plant tissues or plants.

DESCRIPTION OF THE RELEVANT LITERATURE

Crowley et al., *Cell* (1985) 43:633–641, describe the use of an anti-sense construct of the discoidin gene transfected into Dictyostelium to repress expression of endogenous discoidin genes. See also references cited therein. Anti-sense regulation has also been described by Rosenberg et al., *Nature* (1985) 313:703–706; Preiss et al., *Nature* (1985) 313:27–32; Melton, *Proc. Natl. Acad. Sci. USA* (1985) 82:144–148; Izant and Weintraub, *Science* (1985) 229:345–352; and Kim and Wold, *Cell* (1985) 42:129–138. See also, Izant and Weintraub Cell (1984) 36:1007–1075; Pestka et al., *Proc. Natl. Acad. Sci. USA* (1984) 81:7525–7528; Mizuno et al., ibid (1984) 81:1966–1970; Coleman et al., *Cell* (1984) 37:683–691; Travers, *Nature* (1984) 311:410 and Weintraub et al., *Trends in Genetics* (1985) 1:22–25. McGarry and Lindquist, *Proc. Natl. Acad. Sci. USA* (1986) 83:399–403, report the inhibition of heat shock protein synthesis by heat-inducible antisense RNA.

SUMMARY OF THE INVENTION

Regulation of expression in plant cells is achieved by integrating into the plant cell host a DNA sequence comprising a gene in which the transcribed DNA sequences are at least partially complementary to a DNA sequence already transcribed by the host. The exogenous integrated DNA will be under the transcriptional control of a transcriptional initiation region recognized by the plant cell host. Transcription of the exogenous integrated DNA will result in multicopies of an antisense RNA which will be complementary to an endogenous RNA of the host cell. This antisense mRNA will result in reduction of the functioning of the naturally existing RNA.

BRIEF DESCRIPTION OF THE DRAWINGS

FIG. 1 indicates the EcoRI-BamHI fragment from pCGN 1401. This fragment (SEQ. ID NO: 1) corresponds to the 5'-portion of P1 including the region encoding the N-terminus of the mature polygalacturonase protein. The underlined amino acids are predicted from the DNA sequence and agree with the amino acid sequence determined by chemical sequencing from purified polygalacturonase.

DESCRIPTION OF THE PREFERRED EMBODIMENTS

Figure 2A:
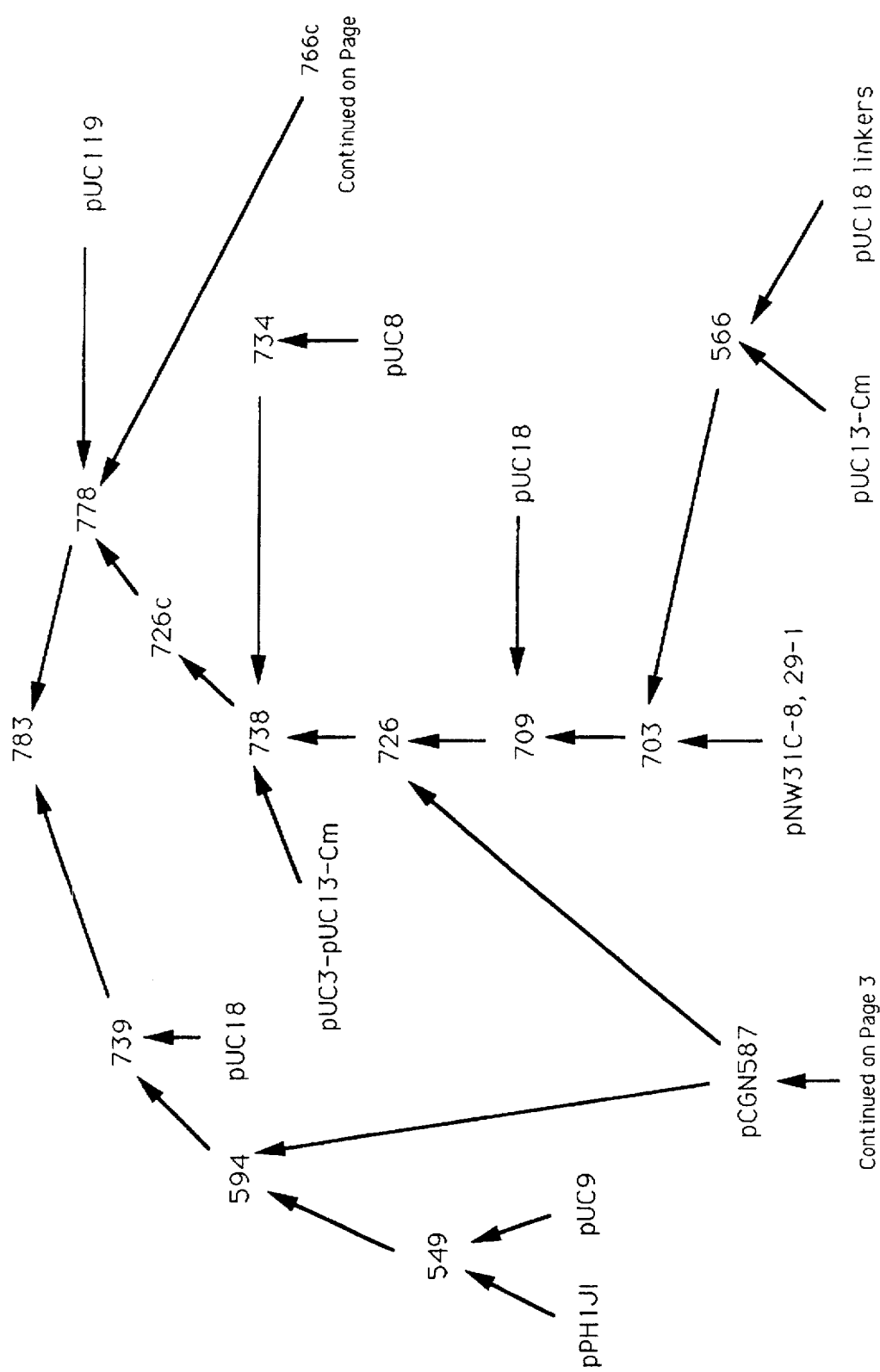
FIG. 2 is a flow chart of the various plasmids used in the construction of the binary vector pCGN783.

Methods and compositions are provided for modulating RNA utilization, particularly modulation of a phenotypic property of a plant host cell. The compositions involve transcription constructs having transcriptional initiation and termination regions separated by a sequence which is complementary to a sequence present on RNA, particularly messenger RNA, endogenous to the host. By this means, various processes endogenous to the plant host cell may be modulated, so that the production of individual proteins may be reduced, multi-enzyme processes modulated, particular metabolic paths modulated or inhibited in preference to one or more other metabolic paths, production of non-proteinaceous products reduced, cell differentiation modified, and the like.

The sequence complementary to a sequence of the messenger RNA will usually be at least about 75 nucleotides, more usually at least about 20 nucleotides, preferably about 30 nucleotides, and more preferably about 50 nucleotides, and may be 100 nucleotides or more, usually being fewer than about 5000 nucleotides, more usually being fewer than 2000 nucleotides, and preferably being fewer than 7000 nucleotides. The sequence may be complementary to any sequence of the messenger RNA, that is, it may be proximal to the 5'-terminus or capping site, downstream from the capping site, between the capping site and the initiation codon and may cover all or only a portion of the non-coding region, may bridge the non-coding and coding region, be complementary to all or part of the coding region, complementary to the 3'-terminus of the coding region, or complementary to the 3'-untranslated region of the mRNA.

The particular site(s) to which the anti-sense sequence binds and the length of the anti-sense sequence will vary depending upon the degree of inhibition desired, the uniqueness of the sequence, the stability of the anti-sense sequence, or the like. Therefore, to some degree, these factors will be determined empirically based on the experience observed with a particular anti-sense sequence.

The sequence may be a single sequence or a repetitive sequence having two or more repetitive sequences in tandem, where the single sequence may bind to a plurality of messenger RNAs. In some instances, rather than providing for homoduplexing, heteroduplexing may be employed, where the same sequence may provide for inhibition of a plurality of messenger RNAs by having regions complementary to different messenger RNAs.

The antisense sequence may be complementary to a unique sequence or a repeated sequence, so as to enhance the probability of binding. Thus, the antisense sequence may be involved with the binding of a unique sequence, a single unit of a repetitive sequence or of a plurality of units of a repetitive sequence. The antisense sequence may result in the modulation of expression of a single gene or a plurality of genes.

The transcriptional construct will be comprised of, in the direction of transcription, a transcriptional initiation region, the sequence coding for the antisense RNA on the sense strand, and a transcriptional termination region.

The transcriptional initiation region may provide for constitutive expression or regulated expression. A large number of promoters are available which are functional in plants. These promoters may be obtained from Ti- or Ri-plasmids, from plant cells, plant viruses or other hosts where the promoters are found to be functional in plants. Illustrative promoters include the octopine synthetase promoter, the nopaline synthase promoter, the manopine synthetase promoter, etc., as illustrative of promoters of bacterial origin functional in plants. Viral promoters include the cauliflower mosaic virus full length (35S) and region VI promoters, etc. Endogenous plant promoters include the ribulose-1,6-biphosphate (RUBP) carboxylase small subunit (ssu), the β-conglycinin promoter, the phaseolin promoter, the ADH promoter, heat-shock promoters, tissue specific promoters, e.g., promoters associated with fruit ripening, etc.

The transcriptional initiation region may be a naturally-occurring region, a RNA polymerase binding region freed of the regulatory region, or a combination of an RNA polymerase binding region from one gene and regulatory region from a different gene. The regulatory region may be responsive to a physical stimulus, such as heat, with heat shock genes, light, as with the RUBP carboxylase SSU, or the like. Alternatively, the regulatory region may be sensitive to differentiation signals, such as the β-conglycinin gene, the phaseolin gene, or the like. A third type of regulatory region is responsive to metabolites. The time and level of expression of the antisense RNA can have a definite effect on the phenotype produced. Thus the promoters chosen will determine the effect of the antisense RNA.

Any convenient termination region may be employed, conveniently the termination region of the RNA polymerase binding region, or a different termination region. Various termination regions are available and the choice is primarily one of convenience, where prior constructions or DNA sequences may be available. Conveniently, the opine termination regions may be employed, or termination regions from endogenous genes, such as the genes which have been described previously.

The various fragments may be joined by linkers, adapters, or the like, or directly where convenient restriction sites are available. The DNA sequences, particularly bound to a replication system, may be joined stepwise, where markers present on the replication system may be employed for selection.

The constructions of the subject invention may be introduced into the host cell in a variety of ways. Of particular interest is the use of *A. tumefaciens* with protoplasts, injured leaves, or other explant tissues. Other techniques which may find use include electroporation with protoplasts, liposome fusion, microinjection, or the like. The particular method for transforming the plant cells is not critical to this invention.

Any plant may be employed in accordance with this invention, including angiosperms, gymnosperms, monocotyledons, and dicotyledons. Plants of interest include cereals such as wheat, barley, maize, triticale, etc.; fruits, such as apricots, oranges, grapefruits, apples, pears, avocados, etc.; nuts, such as walnuts, almonds, filberts, pecans, etc.; vegetables, such as carrots, lettuce, tomatoes, celery, turnips, potatoes, broccoli, asparagus, etc.; woody species, such as poplar, pine, sequoia, cedar, oak, etc; ornamental flowers; or other cash crops, such as tobacco, jojoba, rapeseed, Cuphea, soybeans, sunflower, sugar beet, safflower, etc. For each species, there will generally be different genes to modulate, so as to change the phenotype of the host.

After the cells have been transformed, the cells will be regenerated into plants. Various techniques exist for regenerating plants from cells. Calli can be developed from the cells and the calli induced to form shoots which may then be transferred to an appropriate nutrient medium in soil to regenerate the plant. The plants will then grow and, as appropriate, may be crossed with other plants so as to establish the stability of the change in phenotype over a number of generations. Other techniques may be employed for regenerating the plants without pollination or fertilization. Because those plant genotypes that can be regenerated from culture may not be directly applicable as crop varieties, the transformed plant may be crossed with alternate untransformed germplasm in order to transfer the trait to appropriate breeding lines.

A wide variety of modifications may be made in numerous types of plants. These modifications may include varying the fatty acid distribution of a fatty acid source, such as rapeseed, Cuphea or jojoba, delaying the ripening in fruits and vegetables, changing the organoleptic, storage, packaging, picking and/or processing properties of fruits and vegetables, delaying the flowering or senescing of cut flowers for bouquets, reducing the amount of one or more substances in the plant, such as caffeine, theophylline, nicotine, or altering flower color.

For changing the fatty acid distribution, target species could be coconut and palm trees, Cuphea species, rapeseed, or the like. The target genes of particular interest could be acetyl transacylase, acyl carrier protein, thioesterase, etc.

For varying the amount of nicotine, a target species could be tobacco. The target genes could be N-methylputrescine oxidase or putrescine N-methyl transferase.

For delaying the ripening in fruits, the target species could be tomato or avocado. The target genes could be polygalacturonase or cellulase.

For varying the amount of caffeine, the target species could be coffee (*Coffea arabica*). The target gene could be 7-methylxanthine 3-methyl transferase.

For varying the amount of theophylline, the species could be tea (*Camellia sinensis*). The target gene could be 7-methylxanthine 3-methyl transferase.

For altering flower color the targets could be petunia, roses, carnations, or chrysanthemums, etc. The target genes could be chalcone synthase, phenylalanine ammonia lyase, or dehydrokaempferol (flavone) hydroxylases, etc.

For altering lignin content, the targets could be loblolly pine, Douglas fir, poplar, etc. The target genes could be cinnamoyl-CoA:NADPH reductase or cinnamoyl alcohol dehydrogenase, etc.

In general, reducing the activity of one enzyme at a branch point in a metabolic pathway could allow alteration of the ratios of the products formed.

The transcription construct will usually be joined to a replication system, particularly a bacterial replication system, for manipulation and cloning during its construction. The replication system can be any convenient replication system, particularly one that is functional in E. coli, and one or more markers may be present for detecting transformed bacteria.

Where A. tumefaciens or A. rhizogenes is employed for transferring the DNA, the construction will also be joined to at least one T-DNA border. Thus, the construction will include one T-DNA border, particularly the right T-DNA border, or may be sandwiched between the left and right T-DNA borders.

Various techniques exist for transferring the construct employing the Ti- or Ri-plasmid as the means for the transfer. These techniques include providing for a plasmid which is capable of replication in Agrobacterium where the construct in T-DNA becomes integrated into the Ti- or Ri-plasmid by recombination. Alternatively, binary vectors may be employed, where the Ti- or Ri-plasmid in the Agrobacterium may or may not have a T-DNA region homologous with the T-DNA of the construct. In either event, so long as the vir genes are present on the endogenous plasmid, the T-DNA can be transferred successfully to the plant.

By having a marker as part of the expression construct, particularly antibiotic resistance, such as kanamycin resistance, hygromycin resistance, gentamicin resistance, bleomycin resistance, etc., one can select for those plant cells which have retained the construct in functional form. Where binary vectors are being employed and where the T-DNA in the Ti- or Ri-plasmid of the Agrobacterium retains the oncogenes, one will select for morphologically normal cells, which lack oncogenic expression.

Where electroporation or microinjection is employed, there need be no concern about gall formation and one expects that the morphology of the resulting plants would be normal, except for the modified phenotype.

An example of the use of an anti-sense strand is the regulated modulation of the expression of polygalacturonase (PG) in tomatoes. The ability to reduce the production of polygalacturonase could have a positive effect on the solids content of the tomato plant and improve tomato processing.

To control polygalacturonase expression in tomato fruit a transcription construct is prepared having the anti-sense strand of the polygalacturonase gene transcribed. The entire gene including flanking regions need not be employed, conveniently cDNA or a fragment thereof may be employed. The fragment will be from about 100 to 2000 nt, more usually from 150 to 1000 nt.

The transcription initiation regulatory region is desirably inducible, rather than constitutive, particularly being active at the time of fruit breaking (shortly prior to ripening). For this purpose the polygalacturonase gene transcriptional initiation region may be employed or a transcriptional initiation region of another gene associated with the development of fruit during ripening.

The manner of construction Or the transcription cassette need not be repeated here. Once the construct has been prepared, it is introduced into tomato plant cells in accordance with conventional ways, and plants regenerated from the cells.

The following examples are offered by way of illustration and not by way of limitation.

EXPERIMENTAL

The pCGN978xK12 was deposited at the A.T.C.C. on Mar. 25, 1986, and given Accession No. 67064 and pCGN1401 was deposited on Oct. 7, 1986 at the A.T.C.C. and given Accession No. 67227.

EXAMPLE 1

AroA AntiSense

Materials and Methods

T4 ligase was from ProMega Biotech. Restriction enzymes, Klenow polymerase fragment, and Bal31 were from Bethesda Research Laboratories (BRL).

Construction of the octopine cassette, PCGN1151.

The ocs5'-ocs3' cassette, was inserted into a derivative of pUC8 (Vieira and Messing, Gene (1982) 19:259–268), where a XhoI linker (CCTCGAGG) was inserted at the HincII site and the EcoRI site removed by filling in with the Klenow fragment of DNA polymerase. The octopine synthetase cassette was prepared by linking the XhoI (15208) -BamHI (13774) fragment from the octopine Ti-plasmid pTiA6 (Currier and Nester (1976) J. Bact. 126:157–165; Thomashow et al., Cell (1980) 19:729–739) containing the T-DNA border to the cut-down BamHI (13774) to EcoRI (linker) fragment (the numbering is by Barker, et al., Plant Mol. Biol. (1983) 2:335–350, for the closely related Ti-plasmid pTi15955). The cut-down BamHI-EcoRI fragment was obtained by digesting an EcoRI (13362) to BamHI (13774) subclone of the T-region of pTiA6 with XmnI (13512), followed by resection with Bal31 exonuclease. EcoRI linkers (GGAATTCC) were added and EcoRI to BamHI fragments of approximately 130 bp gel purified, cloned into M13mp9 and sequenced. A clone in which the EcoRI linker was inserted at 13642 between the transcription initiations point and the translation initiation codon was identified by comparison with the sequence of de Greve et al., J. Mol. Appl. Genet. (1982) 1:499–512.

The EcoRI cleavage site was at position 13639, downstream from the mRNA start site. The SmaI site at 11207 was converted to a XhoI site using oligonucleotide linkers (CCTCGAGG) and the 3' end of the octopine gene from the EcoRI (12823) to the converted XhoI site added to the cassette. The resulting expression cassette having the octopine synthetase 5'-region (15208–13639) and 3'-region (12823–11207) was then inserted into the XhoI site of the modified pUC8 to provide pCGN451.

Construction of the aroA Sense/AntiSense Binary Plasmid.

pMG38 (Comai et al., Nature (1985) 317:741–744) was digested with BamHI to provide a fragment containing the aroA gene (nucleotides 1377–2704; Stalker et al., J. Biol. Chem. (1985) 260:4724–4728), which was inserted into the BamHI site of the mas5'-ocs3' cassette, pCGN46 (Comai et al., Nature (1985) 317:741–744) in the antisense (minus orientation) with respect to the mas promoter to provide pCGN964b.

The same aroA gene as described above, as an EcoRI fragment from pPMG38, was inserted into pCGN451 in the octopiney after digestion of pCGN451 with EcoRI resulting in plasmid pPMG45 (osc-aroA).

pCGN525 resulted from combining the large HindIII-BamHI fragment of pACY184 (Chang and Cohen, J. Bact. (1978) 134:1141–1156) with the HindIII-BamHI fragment of the bacterial kanamycin resistance gene from Tn5 (Jorgensen et al., Molec. Gen. Genet. (1979) 177:65–72). The XhoI fragment of PPMG45 was inserted into the SalI site of pCGN525 to provide pCGN963. The HindIII site of pCGN963 was replaced with a XhoI linker (CCTCGAGG)

and the XhoI fragment from PCGN9611 containing the mas-antisense aroA construct was inserted into this new XhoI site. This plasmid, containing both the sense and antisense aroAyis pCGN965.

pCGN978, a binary vector, was constructed by ligating pCGN965 and pRK290 (Ditta et al., *Proc. Natl. Acad. Sci. USA* (1980) 77:7347–7351) after digestion with BglII.
Construction of PPMG511, An aroA Sense Plasmid.

The aroA gene, as a XhoI fragment, from pPMG45 was inserted into pCGN517 digested with SalI to provide pPMG54. pCGN517 is prepared from pHC79 (Hohn and Collins, *Gene* (1980) 11:291–298) with the kanamycin resistance gene of Tn903 from pUC5K (Vieira and Messing, *Gene* (1982) 19:259–268) inserted at the PstI site.
Mating to *Agrobacterium tumefaciens* and Gall Formation.

pCGN978 and pPMG54 were each plate mated with *A. tumefaciens* strain K12 (strain K72 was generated by transforming pTiA6 into strain A114 (NT1); (Sciaky et al., *Plasmid* (19) 1:238–253) and pRK2073 (Leong et al., *J. Biol. Chem.* (1982) 257:8724–8730). The plate-mating protocol is described by Comai et al., *Plasmid* (1983) 10:21–30. Agrobacterium carrying pCGN9788 was selected on AB plates (Chilton et al., *Proc. Natl. Acad. Sci. USA* (1974) 71:3672–3676) plus 200 µg/ml streptomycin and 50 µg/ml kanamycin and the presence of pCGN978 confirmed by Southern analysis. Recombinants with pPMG54 integrated into the T-DNA of K12 were selected on AB plates plus 100 µg/ml kanamycin and confirmed by Southern analysis.

Galls were induced on 3- to 4-month-old Kalanchoe plants by wounding leaves with toothpicks dipped in a solution of pCGN978xK12 and pPMB54XK972 (about $10^9$ bacteria/ml in MG/L broth (Garfinkel and Nester, *J. Bacteriol.* (1980) 194:732–743). Gall material was harvested from four plants for each construct after four weeks and frozen at −70° C. until use. The gall material was randomized for each construct and analyzed for aroA protein by Western analysis.

The Western analysis was performed aroA of pPMB54xK12 and 3.0 g of pCGN978xK12 gall tissue were ground in liquid nitrogen. 0.3 g/g tissue of polyvinylpyrrolidone was added. The tissue was suspended in 1.5 ml/g tissue of 0.1M sodium citrate, pH 5.6, 10 mM EDTA, 0.15M NaCl, 0.05% Nonidet P-40, 25 mg/ml bovine serum albumin (BSA), 1 mM dithiothreitol, 1 mM phenylmethylsulfonyl fluoride (PMSF), 10 µm leupeptin (Sigma) and 10 mM thiourea. The homogenate was centrifuged at 15,000 g for 15 min at 4° C. 25 µl of antiserum, prepared by injecting purified 3-enolpyruvylshikimate phosphate (EPSP) synthase into rabbits and 125 µl 10% (w/v) suspension of *S. aureus* (Calbiochem) were added to each supernatant and incubated with agitation for 1 h at room temperature.

Samples were then centrifuged (5000×g, 5 min) and the pellet washed twice with 50 mM Tris, pH 7.5 1 mM EDTA, 0.5M NaCl and 0.05% Nonidet P-40. The resulting pellets were suspended in 100 µl 0.125M Tris, pH 6.8, 4% SDS, 20% glycerol and 10% 2-mercaptoethanol and heated for 2 min at 90° C. The entire sample was then electrophoresed on a 10% acrylamide gel. The resolved peptides were transferred to nitrocellulose (BA85, Schleicher and Schuell) as described by Burnette, *Anal. Biochem.* (1987) 112:195–203) at 100 V for 3 hr in a Hoefer TE42 transfer unit. Nitrocellulose filters were then incubated in BLOTTO (20 mM Tris, pH 7.5, 5% dehydrated skim milk, 0.5M NaCl, 0.1% antifoam A, 10 mM Na Azide) for 1 hr at room temperature, followed by an overnight incubation at 4° C. in BLOTTO containing a 1:50 dilution of anti-EPSP synthase serum. Filters were washed for 10 min in 20 mM Tris, pH 7.5, 150 mM NaCl, for 20 min in the same buffer containing 0.05% Tween-20 and for another 10 min in buffer without detergent. BLOTTO containing $10^6$ cpm/ml of $^{125}$I-labeled protein A (9 µCi/mg; NEN) was then added to filters and incubated at room temperature for 2 hr. The filters were washed overnight in 50 mM Tris, pH 7.5, 1M NaCl and 0.4% lauryl sarcosine and then washed for 3 hr at room temperature in 50 mM Tris, pH 7.5, 5 mM EDTA, 150 mM NaCl, 0.5% Triton X-100, and 0.1% SDS. After rinsing and drying, filters were exposed to Kodak XAR X-ray film at −70° C. using a DuPont Lightning Plus intensifying screen.

The pCGN978 containing gall showed only 10–20% of the activity of the control pPMG54 galls. Earlier comparisons of the expression of aroA in the binary system versus the integrated system showed that the binary system is only 70–80% as efficient as the integrated system. Therefore, an overall decrease in aroA activity of 60% is observed where the anti-sense construct is also present.

Experimental for Electroporation Experiments
Plasmid Constructions.

The anti-sense 5'mas-aroA-3'ocs construct, pCGN964b, was constructed as described above. The sense 5'mas-aroA-3'ocs construct, pCGN964a, was obtained from the same ligation, with the sense orientation being selected.
Plant material.

Protoplast donor plants of *Nicotiana tabacum* cv. Xanthi were grown in glass jars under aseptic conditions as described elsewhere (Facciotti and Pilet, 1979). Apical shoots were placed in 100 ml of agar medium (Murasahige and Skoog (MS) medium) containing 0.7% Gibco Phytagar, 30 g/l sucrose, 1.0 mg/l IAA and 0.15 mg/l Kinetin, adjusted to pH 5.55 prior to autoclaving). The cultures were kept at 23±2° C. under a 12 hr dark/light regime.

The following steps were performed under aseptic conditions with sterile solutions.

Young leaves were removed from 4–5 week old plants during the dark portion of the cycle. The main veins were discarded, and the remaining leaf tissue was cut once longitudinally. These leaf sections were infiltrated (to 200 militorr) with a 6% sorbitol solution containing 0.4% pectinase (Pectolyase Y-23, Seishin Pharmaceutical Co. Ltd., Japan) and 0.6% cellulase (Onozuka RS, Yakult Pharmaceutical Industry Co. Ltd., Japan). After 2–3 hr incubation, the macerate was gently pipetted to release protoplasts and passed through a 52 µ nylon filter. The protoplasts were pelleted by centrifugation at 50×g, and washed twice with 7% sorbitol solution. Protoplast density was determined by use of a hemacytometer (using a 1 mm, 9 square grid, the average of the squares counted multiplied by $10^4$ yields an estimate of the total number of protoplasts per ml). Based on the calculated density, protoplasts were suspended at a final density of 2.2–3.0 million per ml in buffer (buffer containing: 10 mM Hepes pH 7.1, 140 mM NaCl, 5 mM CaCl2 and 6% sorbitol).
Electroporation.

Protoplasts suspended in buffer were divided into 1 ml aliquots. To each aliquot 1 mg of carrier DNA (in the form of herring sperm DNA) was added. Following the addition of carrier DNA, plasmid DNA was added in the desired concentrations. The protoplast/DNA mixture was incubated for 5 min prior to electroporation and subsequently transferred to 1 ml aluminum foil lined plastic cuvettes for electroporation. The electroporation pulse was delivered by a 1250 µF capacitor charged to 150 volts. The pulse duration was measured through the buffer solution, devoid of protoplasts, and found to be 40 msec. Following electroporation the protoplasts were incubated for 10 min at room temperature in the cuvette, and subsequently transferred to Petri plates, diluted with 10 ml of protoplast culture media (MS salts containing 0.6 mg/l NAA, 0.2 mg/l 2,4-D, 0.8 mg/l Kinetin, 5.5% sorbitol and 30 g/l sucrose) and cultured at 23±2° C. in complete darkness. After 48–50 hr the protoplasts were harvested by gentle centrifugation (50×g for 6 min), the supernatant removed and protoplasts frozen in liquid nitrogen and stored at −70° C. At a later date the frozen protoplast pellet was suspended in 1 ml of extraction buffer for Western analysis (containing: 0.1M Na Citrate, 10 mM EDTA, 150 mM NaCl, 0.05% Nonidet, 25 mg/ml BSA, 1 mM PMSF, 10 mM DTT, 10 mM thiourea, 10 μM leupeptin). 0.05 g/ml polyvinylpyrroldidone (PolyClarAT, BDH) was added and the mixture ground for 30 sec in a Polytron homogenizer. The supernatant was collected and Western analysis performed as described above.

Experiments.

Experimental treatments utilized pCGN964a and pCGN964b (see section on Plasmid construction for details of each construct). In each experiment treatments containing both 964a and 964b were compared to treatments containing 964a or 964b alone:

| | |
|---|---|
| 50μ 964a | 0μ 964b |
| 50μ 964a | 10μ 964b |
| 50μ 964 | 25μ 964b |
| 50μ 964a | 50μ 964b |
| 50μ 964a | 100μ 964b |
| 0μ 964a | 50μ 964b |

In all cases the addition of the anti-sense DNA (964b) reduced the protein level detected by Western analysis (compared to levels obtained with 964a alone). The reduction in level averaged 50%. No protein was detected in 964b alone, as expected.

EXAMPLE 2

Polygalacturonase Antisense Construct.

Bacterial Strains.

TABLE I

Bacterial Strains

| Escherichia Coli Designation | Phenotype | Origin/Reference |
|---|---|---|
| 7118 | Δlac | Vieira and Messing Gene (1982) 19: 259–268 |
| Y1088 | hsdR-hsdM+ | Young and Davis PNAS (USA) (1983) 80: 1194–1198 |
| Y1090 | Δlon | |
| C2110 | polA | Stalker et al. PNAS (USA) (1983) 80: 5500–5504 |

Enzymes and Radioisotopes

All enzymes were obtained from commercial sources and used according to the manufacturer's suggestions. Radioisotopes were obtained from New England Nuclear.

Isolation of poly(A)+RNA

Ripe fruit of tomato cv. CaliGrande was harvested and frozen in liquid $N_2$. Frozen tissue was ground in a mortar and pestle in liquid $N_2$, and the resulting powder was extracted by homogenization with a Brinkman polytron in buffer as described by Facciotti et al., Bio/Technology (1985) 3:241–246. Total RNA was prepared as described by Colbert et al., Proc. Natl. Acad. Sci. (USA) (1983) 80:2248–2252.

Polysaccharides were precipitated from total RNA preparations with 40 mM sodium acetate and 0.5 vol ethanol (Mansson et al. (1985) Mol. Gen. Genet. (1985) 200:356–361. Poly(A)+RNA was isolated as described by Maniatis et al. (1982) Molecular Cloning: A Laboratory Manual, Cold Spring Harbor, N.Y.

Synthesis of cDNA

Synthesis of cDNA from poly(A)+RNA was performed as described by Gubler and Hoffman, Gene (1983) 25:263–269 with the following modifications: The reaction mixture for synthesis of the first strand included 1 mM dGTP, 1 mM dATP, 1 mM TTP, 0.5 mM dCTP, 0.5 unit/μl RNasin (Promega), 4 μ of tomato poly(A)+RNA, and 80–100 units of reverse transcriptase (Life Sciences). The reaction was stopped with 2 μl of 500 mM EDTA, then precipitated with 10 μg tRNA, 1 vol 4M $NH_4OAc$, and 2.5 vol of ethanol overnight on dry ice.

Second strand synthesis was performed from approximately 500 ng of the first strand reaction product. Aliquots of the first and second strand reaction mixtures were radiolabeled separately with 20 μCi of 5'-[α-$^{32}$P] dCTP to monitor each reaction independently.

Cloning of Double-Stranded cDNA in λgt11.

The double-stranded cDNA was EcoRI methylated as described by the manufacturer (New England Biolabs). After ethanol precipitation, the cDNA ends were blunted using 3 units of the Klenow fragment of DNA polymerase I (Bethesda Research Laboratories) under the following conditions: 66 mM Tris-HCl pH 7.5, 20 mm $MgCl_2$, 100 mM dithiothreitol, 100 μM dGTP, dATP, TTP, and dCTP at room temperature for 1 hr. The DNA was then ethanol precipitated. After blunting, 2 μg Of EcoRI phosphorylated linkers were added to the cDNA in 10 μl of ligase buffer (50 mM Tris, pH 7.5, 10 mM $MgCl_2$, 20 mM dithiothreitol, 1 mM ATP, and 5 mg/ml bovine serum albumin). $T_4$ DNA ligase (1 Weiss unit, Weiss, J. Biochem, (1968) 243:4543, Promega) was added and incubated for 6 hr at 15° C. An additional Weiss unit of $T_4$ DNA ligase in 10 μl of ligase buffer was then added and incubated for 24 hr at 15–19° C. The reaction was phenol extracted, ethanol precipitated and digested with 100 units EcoRI (New England Biolabs) for 6–8 hrs, phenol extracted and ethanol precipitated. Excess linkers and cDNA of fewer than 500 base pairs were removed by chromatography on Bio-gel A-50 m (100–200 mesh) and the sized cDNA was ligated to EcoRI-cleaved λgt vector DNA (Statagene) as described by Huynh et al. in DNA Cloning: A Practical Approach, (ed. D. M. Glover), pp. 49–78, IRL Press, Oxford, England, 1985.

In vitro packaging reactions were performed with Gigapack extracts (Stratagene) as described by the vendor. Initial test ligations and in vitro packaging were done using various dilutions of cDNA to empirically determine the optimal ration of cDNA/vector for production of recombinant phage. The packaged λgt11 phage were plated on E. Coli Y1088 in the presence of isopropyl-1-thio-β-D-galactoside (IPTG) and 5-bromo-4-cloro-3-indolyl-β-D-galactoside (X-gal) as described by Huynh et al. (1985), supra to determine the number or recombinants. Greater than 5×10$^6$ recombinants at a 90% insertion rate was obtained in λgt11.

Library Screening

Approximately 200,000 phage from an unamplified λgt11 library were screened at a density of 20,000 plaque-forming units per 9 cm square plate using E. coli Y1090 as the host as described by Huynh et al. (1985) supra, except that NZY media (per liter: 5 g NaCl, 2 g $MgCl_2$, 10 g NZamine type A (Sheffield Products), 5 g yeast extract and 15 g agar) was used. Plates were incubated and overlaid with nitrocellulose sheets containing IPTG as described by Huynh et al. (1985), supra. The nitrocellulose sheets were saturated with 0.5M Tris pH 8.0, 0.15M NaCl, 0.02% $NaN_3$, 0.1% Triton X-100 and 5% non-fat dry milk, then incubated 30 min at room temperature with the same buffer containing anti-polygalacturonase2 antibody (see below) diluted 1:1000. Bound antibody was detected with an alkaline phosphatase-conjugated second antibody (Promega) as described by the vendor. Positive plaques were purified by successive plating and phage DNA was prepared as described (Maniatis et al. (1982) supra.

Subcloning and Sequencing of cDNA Insert P1

Phage DNA from positive plaque P1 was digested with EcoRI and the resulting fragment was subcloned in EcoRI-digested vector M13 Blue Scribe Minus (Stratagene) by in vitro ligation. Initial DNA sequencing was performed using a single-stranded template from the Blue Scribe construct prepared as described by the manufacturer. All DNA sequencing was performed as described by Sanger et al., *Proc. Natl. Acad. Sci. (USA)* (1977) 74:5463 or Maxam and Gilbert, *Methods Enzymol.* (1980) 65:499–580. Overlapping sequences were obtained by subcloning purified BamHI-EcoRI, HindIII-EcoRI, and BamHI-HindIII fragments (Maniatis et al., (1982) supra) from the Blue Scribe construct into M13mp18 (Yanisch-Perron et al., *Gene* (1985) 53:103–119) and M13mpf9 (Norrander et al., *Gene* (1983) 26:101–106).

Polygalacturonase Purification for Protein Sequencing

Total cell wall bound proteins were prepared from ripe fruit of cv. CaliGrande as described by Crookes and Grierson, *Plant Physiol.* (1983) 72:1088–1093. The extract was dialyzed against 0.025M ethanolamine, pH 9.4, and applied to a 9×300 mm column of chromatofocusing exchanger PBE 94 (Pharmacia) equilibrated with 0.025M ethanolamine, pH 9.4. Bound proteins were eluted with Polybuffer 96, pH 8.0 (Pharmacia). Fractions containing polygalacturonase were pooled and precipitated with ammonium sulphate (90% saturation) and further fractionated by chromatography over a hydroxyapatite (HAPT) HPLC column. Two ml volumes were layered onto the column and chromatographed at 1 ml/min using a linear gradient extending from 10 mM to 350 mM sodium phosphate, pH 6.8. Samples were monitored at $A_{280}$ and fractionated into 0.5 ml volumes. Fractions collected from numerous runs which contained polygalacturonase were pooled and dialyzed against 6% acetic acid, then lyophilized.

Protein Sequencing

Polygalacturonase prepared as described above was sequenced intact with a Beckman 890 M Liquid Phase Amino Acid Sequencer. The following N-terminal sequence was obtained: Gly-ile-lys-val-ile-asn.

Polygalacturonase Purification for Antibody Production

Tomato cell wall bound proteins were prepared from ripe fruit of cv. UC82B as described by Tucker and Grierson, *Planta* (1982) 155:64–67. The pellet from ammonium sulphate precipitation was dissolved in 150 mM NaCl and then dialyzed overnight against the same buffer.

The protein solution was then fractionated on a TSK 3000/2000 HPLC sizing column using an isocratic gradient containing 10 mM NaCl and 10 mM Tris pH 7.2 at a flow rate of 0.5 ml/min.

TSK fractions containing polygalacturonase activity (Reisfeld et al., *Nature* (1962) 195:281–283) were pooled and further fractionated over an hydroxyapatite HPLC column using a linear gradient of 10 mM–350 mM sodium phosphate, pH 6.8 and a flow rate of 1 ml/min. The peak containing polygalacturonase activity was collected and used to inject rabbits for antibody production.

Polygalacturonase for booster injections was prepared by resolving the cell wall bound protein preparation on SDS polyacrylamide gels. The material precipitated with ammonium sulphate (see above) was electrophoresed on 3 mm thick and 14 mm wide gels containing 12.5% polyacrylamide (Laemmli, *Nature* (1970) 227:680–685) and proteins were visualized by staining with Coomassie Brilliant Blue R. The region corresponding to the polygalacturonase bands (approximately 40,000–43,000 daltons) was excised, frozen, and ground with liquid $N_2$.

Antibody Preparation

One rabbit was given 4 injections of polygalacturonase (125 µg injection) over a one month period. The same rabbit was then given a booster injection of polygalacturonase (approximately 150 µg) recovered from SDS polyacrylamide gels. An identical booster injection was again Ogiven one week after the first. The animal was exsanguinated 2 weeks later as a source of serum.

Six ml of the crude serum were diluted with 6 ml of 0.1M sodium phosphate, pH 7.0, and applied to a 6 ml column of Protein A-Sepharose (Sigma). The column was washed with 80 ml of 0.1M sodium phosphate, pH 7.0, and the IgG fraction was then eluted with 0.1M glycine, pH 3.0. Fractions with the highest $A_{280}$ were pooled, dialyzed against 20 mM sodium phosphate pH 7.6, 150 mM NaCl and concentrated on an Amicon XM80 membrane. Glycerol was then added to a final concentration of 40%.

Affinity purified antiserum was prepared by incubating the IgG fraction with polygalacturonase linked to a Tresacryl (Pharmacia) affinity chromatography matrix as described by the vendor. Polygalacturonase purified for protein sequencing was linked to 4 ml of Tresacryl resin as described by the manufacturer. Five ml of IgG prepared as described above was diluted to 50 ml with 0.01M Tris pH 7.5, 150 mM NaCl and 0.1% Tween-20 (TBST) and incubated with the resin overnight at 4° C. The resin was then washed with TBST and eluted with 0.2M glycine, pH 2.75. Fractions with $A_{280}$ were pooled and dialyzed against 10 mM Tris pH 8.0, 150 mM NaCl. The final volume of purified antibody was 12 ml representing a 1:2 dilution of the original serum.

RESULTS

Identification of Polygalacturonase cDNAs

Twelve putative polygalacturonase clones were identified from the λgt11 library by reaction with the antibody preparation described above. Using inserts purified from two of the clones as probes, Northern analysis demonstrated that one clone (C3) encoded mRNA expressed during tomato development in the manner and size expected for polygalacturonase mRNA.

To identify additional putative cDNA clones encoding polygalacturonase, phage DNA was prepared from the remaining 10 clones, digested with EcoRI and HindIII, and subjected to Southern blot hybridization analysis (Maniatis et al. (1982) supra) using clone C3 insert as a probe. An additional cDNA clone (P1) crosshybridized to C3 and was further characterized to provide sequences for antisense expression. The identity of P1 as a polygalacturonase cDNA clone was confirmed by comparison of the amino acid sequence predicted from the DNA sequence to the actual polygalacturonase protein sequence. The clone encodes a portion of the polygalacturonase gene beginning approximately at the N-terminus of the mature polygalacturonase polypeptide and extending to the carboxy terminus including the 3' untranslated region.

Construction of the Antisense Polygalacturonase Binary Plasmid

Phage P1 DNA was digested with EcoRI and the cDNA insert was ligated in EcoRI-digested M13 Blue Scribe Minus (Stratagene) to yield pCGN1401.

pCGN1401 was digested with BamHI and EcoRI to provide a 219 bp fragment (FIG. 1) which includes 7 bases (GAATTCC) of the EcoRI linker, 2 bases of the polygalacturonase leader sequence (AT), the triplet encoding the N-terminal amino acid of the mature polygalacturonase protein (GGG) and 210 additional bases to the BamHI site. This fragment was inserted in the unique BamHI-EcoRI site of the mas5'-ocs3' cassette, pCGN46 (Comai et al., Nature (1983) 317:741–744). This resulted in insertion of the fragment in the antisense (minus orientation) to the mas promoter to yield pCGN1402.

pCGN1402 was then digested with the restriction enzyme XhoI and cloned into the unique SalI site of the binary plasmid pCGN783 containing a plant kanamycin resistance marker between the left and right borders. This results in pCGN1403. This plasmid in E. coli C2110 was conjugated into Agrobacterium tumefaciens containing a disarmed Ti plasmid capable of transferring the polygalacturonase antisense cassette and the kanamycin resistance cassette into the plant host genome.

The Agrobacterium system which is employed is A. tumefaciens PC2760 (G. Ooms et al., Plasmid (1982) et al., Nature (1983) 303:179–181; European Patent Application 84-200239.6, 2424183).

Figure 2B:
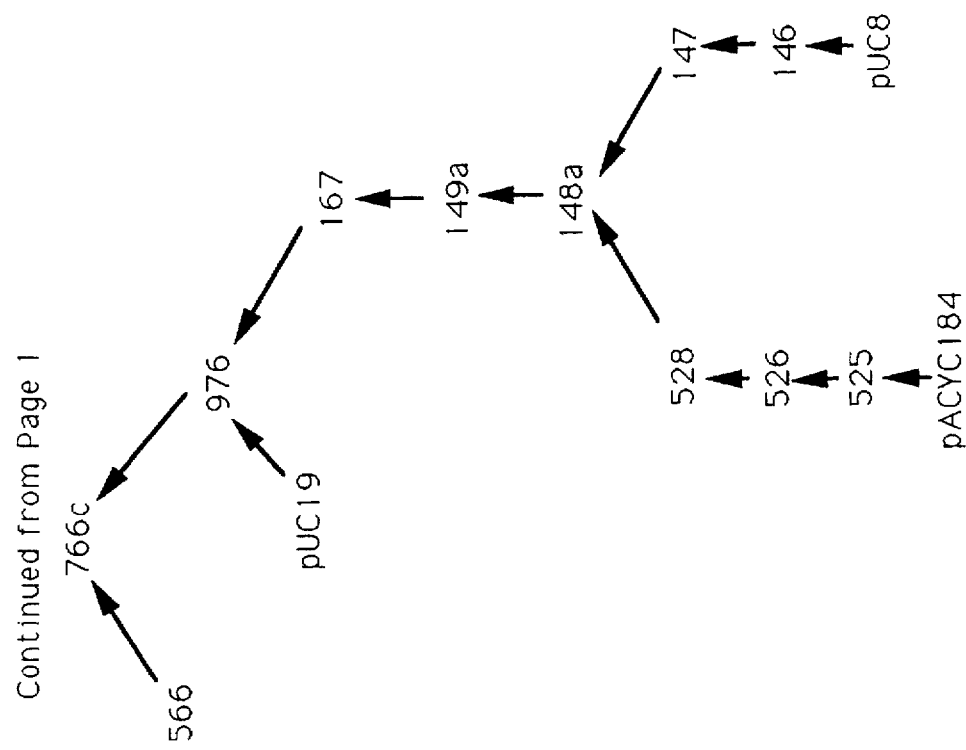
Figure 2C:
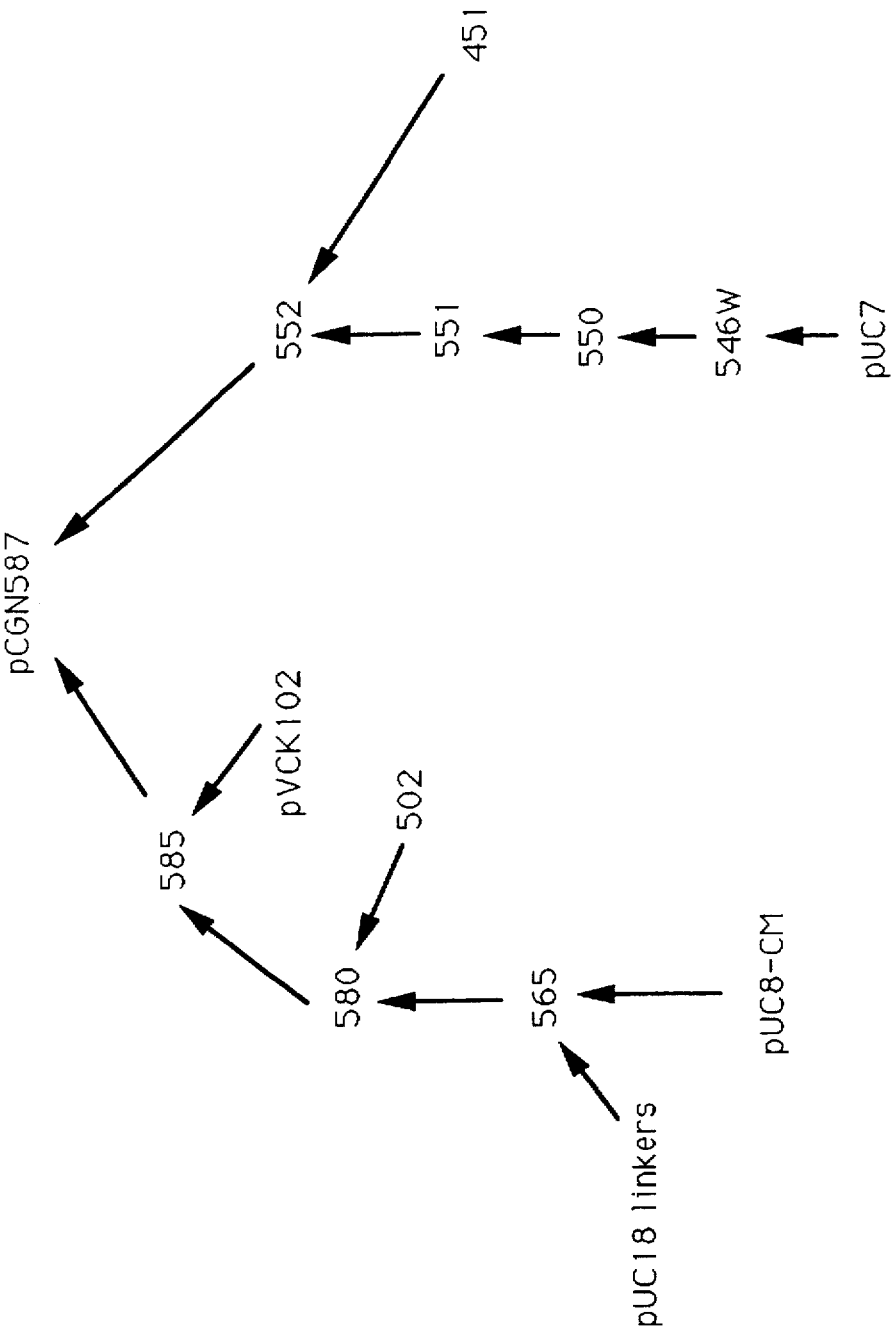

Construction of pCGN783 pCGN783 is a binary plasmid containing the left and right T-DNA borders of Agrobactrium tumefaciens octopine Ti-plasmid pTiA6 (Currier and Nester (1976) supra) the gentamycin resistance gene of pPH1JI (Hirsch et al., Plasmid (1984) 12:139–141), the 35S promoter of cauliflower mosaic virus (CaNV) (Gardner et al., Nucleic Acid Res. (1987) 9:1871–1880); the kanamycin resistance gene of Tn5 (Jorgensen, Mol. Gen. (1979) 177:65); and the 3' region from transcript 7 of pTiA6 (Currier and Nester (1976), supra). The construction of pCGN783 is outlined in FIG. 2.

Construction of pCGN739 (Binary Vector)

To obtain the gentamicin resistance marker, the resistance gene was isolated from a 3.1 kb EcoRI-PstI fragment of pPHIJI (Hirsch et al. (1984), supra) and cloned into pUC9 (Vieira et al., Gene (1982) 19:259–268) yielding pCGN549.

The pCGN549 HindIII-BamHI fragment containing the gentamicin resistance gene replaced the HindIII-BglIII fragment of pCGN587 (for construction, see infra) creating pCGN594.

The pCGN594 HindIII-BamHI region which contains an ocs-kanamycin-ocs fragment was replaced with the HindIII-BamHI polylinker region from pUC18 (Yanisch-Perron, (1985), supra) to make pCGN739.

Construction of 726c (1ATG-Kanamycin-3' region)

pCGN566 contains the EcoRI-HindIII linker of pUC18 (Yanisch-Perron, ibid) inserted into the EcoRI-HindIII sites of pUC13-cm (K. Buckley, Ph.D. thesis, UC-San Diego, 1985). The HindIII-BglHI fragment of pNW31c-8, 29-1 (Thomashow et al. (1980) Cell 19:729) containing ORF1 and 2 (Barker et al. (1983), supra) was subcloned into the HindIII-BamHI sites of pCGN566 producing pCGN703.

The Sau3A fragment of pCGN703 containing the 3' region of transcript 7 from pTiA6 (corresponding to bases 2396–2920 of pTi15955 (Barker et al. (1983), supra) was subcloned into the BamHI site of pUC18 (Yanisch-Perron et al. (1985), supra) producing pCGN709.

The EcoRI-SmaI polylinker region of pCGN709 was replaced with the EcoRI-SmaI fragment from pCGN587 (for production see infra) which contains the kanamycin resistance gene (APH3'II) producing pCGN726.

The EcoRI-SalI fragment of pCGN726 plus the BglII-EcoRI fragment of pCGN734 are inserted into the BamHI-SalI sites of pUC8–pUC13-cm (chloramphenicol resistant, K. Buckley, PhD. Thesis, UC-San Diego, 1985) producing PCGN738. To construct pCGN734, the HindIII-SphI fragment of pTiA6 corresponding to bases 3390–32111 (Barker et al. (1983), supra) was cloned into the HindIII-SphI site of M13mp19 (Norrander et al. (1983), supra). Using an oligonucleotide corresponding to bases 3287 to 3300, DNA synthesis was primed from this template. Following S1 nuclease treatment and HindIII digestion, the resulting fragment was cloned into the HindIII-SmaI site of pUC19 (Yanisch-Perron et al. (1985), supra). The resulting EcoRI-HindIII fragment corresponding to bases 3287–3390 (Barker et al. (1983), supra) was cloned with the EcoRI to HindIII fragment of pTiA6 (corresponding to bases 3390–4494) into the EcoRI site of pUC8 (Vieira and Messing (1982), supra) resulting in pCGN734. pCGN726c is derived from pCGN738 by deleting the 900 bp EcoRI-EcoRI fragment.

Construction of pCGN766c (35S promoter-3' region)

The HindIII-BamHI fragment of pCGN167 (for construction see infra) containing the CaMV-35S promoter, 1ATG-kanamycin gene and the BamHI fragment 19 of pTiA6 was cloned into the BamHI-HindIII sites of pUC19 (Norrander et al. (1983), supra; Yanisch-Perron et al. (1985), supra) creating pCGN976.

The 35S promoter and 3' region from transcript 7 was developed by inserting a 0.7 kb HindIII-EcoRI fragment of pCGN976 (35S promoter) and the 0.5 kb EcoRI-SalI fragment of pCGN709 (transcript 7:3', for construction, see supra) into the HindIII-SalI sites of pCGN566 creating pCGN766c.

Final Construction of pCCN783

The 0.7 kb HindIII-EcoRI fragment of pCCN766c (CaMV-3SS promoter) was ligated to the 1.5 kb EcoRI-SalI fragment of pCGN726c (1-ATG-KAN-31 region) into the HindIII-SalI sites of pUC119 (J. Vieira, Rutgers University, N.J.) to produce pCGN778.

The 2.2 kb region of pCGN778, HindIII-SalI fragment containing the CaMV 35S promoter (1-ATG-KAN-3' region) replaced the HindIII-SalI polylinker region of pCGN739 to produce pCGN783.

pCCN587 was prepared as follows: The HindIII-SmaI fragment of Tn5 containing the entire structural gene for APH3'II (Jorgensen et al., Mol. Gen. Genet. (1979) 177:65), was cloned into pUC8 (Vieira and Messing, Gene (1982), 19:259), converting the fragment into a HindIII-EcoRI fragment, since there is an EcoRI site immediately adjacent to the SmaI site. The PstI-EcoRI fragment containing the 3'-portion of the APH3'II gene was then combined with an EcoRI-BamHI-SalI-PstI linker into the EcoRI site of pUC7 (pCGN546W). Since this construct does not confer kanamycin resistance, kanamycin resistance was obtained by inserting the BglII-PstI fragment of the APH3'II gene into the BamHI- PstI site (PCCN546X). This procedure reassembles the APH3'II gene, so that EcoRI sites flank the gene. An ATG codon was upstream from and out of reading frame with the ATG initiation codon of APH3'II. The undesired ATG was avoided by inserting a Sau3A-PstI fragment from the 5'-end of APH3'II, which fragment lacks the superfluous ATG, into the BamHI-PstI site of pCGN546W to provide plasmid pCGN550. The EcoRI fragment of pCGN550 containing the APH3'II gene was the then cloned into the EcoRI site of pUC8–pUC13 (K. Buckley (1985), supra) to give pCGN551.

Each of the EcoRI fragments containing the APH3'II gene was then cloned into the unique EcoRI site of pCGN451, which contains an octopine synthase cassette for expression, (as described in Example 1) to provide pCGN548 (2ATG) and pCGN552 (1ATG). The plasmid pCGN457 having the ocs 5' and the ocs 3' in the proper orientation was digested with EcoRI and the EcoRI fragment from pCGN551 containing the intact kanamycin resistance gene inserted into the EcoRI site to provide pCGN552 having the kanamycin resistance gene in the proper orientation. This ocs/KAN gene was used to provide a selectable marker for the trans type binary vector pCGN587.

The 5' portion of the engineered octopine synthase promoter cassette consists of pTiA6 DNA from the XhoI at bp 15208–13644 (Barker et al. (1983), supra), which also contains the T-DNA boundary sequence (border) implicated in T-DNA transfer. In the plasmid pCGN587, the ocs/KAN gene from pCGN552 provides a selectable marker as well the right border. The left boundary region was first cloned in M13mp9 as a HindIII-SmaI piece (pCGN502) (base pairs 602–2212) and recloned as a KpnI-EcoRI fragment in pCGN565 to provide pCGN580. pCGN565 is a cloning vector based on pUC8-Cm, but containing pUC18 linkers. pCGN580 was linearized with BamHI and used to replace the smaller BglI fragment of pVCK102 (Knauf and Nester, Plasmid (1982) 8:45), creating pCGN585. By replacing the smaller SalI fragment of pCGN585 with the XhoI fragment from pCGN552 containing the ocs/KAN gene, pCGN587 was obtained.

To construct pCGN167, the AluI fragment of CaMV (bp 7144–7735) (Gardner et al., Nucl. Acids Res. (1987) 9:2871–2888) was obtained by digestion with AluI and cloned into the HincII site of M13mp7 (Vieira Gene (1982) 19:259) to create C614. An EcoRI digest of C614 produced the EcoRI fragment from C614 containing the 35S promoter which was cloned into the EcoRI site of pUC8 (Vieira et al., Gene (1982) 19:259) to produce PCGN146. To trim the promoter region, the BglII site (bp 7670) was treated with BglII and Bal31 and subsequently a BglII linker was attached to the Bal31 treated DNA to produce pCGN147.

pCGN148a containing a promoter region, selectable marker (KAN with 2 ATG's) and 3' region was prepared by digesting pCGN528 (see below) with BglII and inserting the BamHI-BglII promoter arrangement from pCGNf147. This fragment was cloned into the BglII site of pCGN528 so that the BglII site was proximal to the kanamycin gene of pCGN528.

The shuttle vector used for this construct, pCGN528, was made as follows. pCGN525 was made by digesting a plasmid containing Tn5 which harbors a kanamycin gene (Jorgenson et al., Mol. Gen. Genet. (1979) 177:65) with HindIII-BamHI and inserting the HindIII-BamHI fragment containing the kanamycin gene into the HindIII-BamHI sites in the tetracycline gene of pACYC184 (Chang & Cohen J.

Bacteriol. (1978) 134:1141–1156). pCGN526 was made by inserting the BamHI fragment 19 9f pTiA6 (Thomashow et al., Cell (1980) 19:729–739) into the BamHI site of pCGN525. pCGN528 was obtained by deleting the small XhoI fragment from pCGN526 by digesting with XhoI and religating.

pCGN149a was made by cloning the BamHI kanamycin gene fragment from pMB9KanXXI into the BamHI site of pCGN148a.

pMB9KanXXI is a pUC4K variant (Vieira & Messing, Gene (1982) 19:259:268) which has the XhoI site missing but contains a functional kanamycin gene from Tn903 to allow for efficient selection in Agrobacterium.

pCGN149a was digested with BglII and SphI. This small BglII-SphI fragment of pCGN149a was replaced with the BamHI-SphI fragment from MI (see below) isolated by digestion with BamHI and SphI. This produces PCGN167, a construct containing a full length CaMV promoter, 1ATG-kanamycin gene, 3' end and the bacterial Tn903-type kanamycin gene. MI is an ECORI fragment from pCGN550 (see construction of pCGN587) and was cloned into the ECORI cloning site of M13mp9 in such a way that the PstI site in the 1ATG-kanamycin gene was proximal to the polylinker region of M13mp9.

It is evident from the above results that it is possible to modulate expression of a gene in the genome of a plant host by providing for transcription of a sequence complementary to the messenger RNA of a gene expressed in the host. In this manner, various processes can be modified or controlled, resulting in enhancement of production of particular products, changes in cellular differentiation and development, inhibition of formation of products, changes in phenotype, or the like. The use of the anti-sense control can provide for substantial inhibition or varying degrees of reduction of expression of a particular product. In this manner, cellular phenotypes can be modified without the production of extraneous proteins and with particular targeting to a specific gene.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for reducing expression of a gene endogenous to a plant cell, said method comprising:

integrating into the genome of a plant cell a construct comprising in the 5'-3' direction of transcription, a promoter functional in said plant cell, a dsDNA sequence wherein the transcribed strand of said dsDNA is complementary to RNA endogenous to said cell, and a termination region functional in said cell whereby a transformed cell is obtained; and growing said transformed plant cell, whereby said complementary strand is transcribed and binds to said RNA endogenous to said cell, thereby reducing expression of said gene endogenous to said plant cell.

2. A method according to claim 1, wherein said plant cell is dicotyledonous.

3. A method according to claim 2, wherein said reducing results in alteration of a phenotypic trait.

4. A method according to claim 2, wherein said endogenous RNA is messenger RNA.

5. A method according to claim 2, wherein said construct further comprises at least the right T-DNA border.

6. A method according to claim 2, wherein said transformed plant cell is grown into differentiated plant tissue.

7. A method according to claim 2, wherein said promoter provides for regulated expression.

8. A method according to claim 2, wherein the amount of RNA transcribed from said complementary strand present in said cell is less than the amount of said RNA endogenous to said cell.

9. A method according to claim 2, further comprising the step of recovering seed from a plant resulting from a cross between a first plant grown from said transformed plant cell and a second plant.

10. A method for reducing expression of a gene indigenous to a dicotyledonous plant cell, said method comprising:

integrating into the genome of a dicotyledonous plant cell a construct comprising in the 5'-3' direction of transcription, a promoter functional in said plant cell, a dsDNA sequence wherein the transcribed strand of said dsDNA is complementary to RNA indigenous to said cell, and a termination region functional in said cell whereby a transformed cell is obtained; and growing said transformed plant cell, whereby said complementary strand is transcribed and binds to said RNA indigenous to said cell, thereby reducing expression of said gene indigenous to said plant cell.

11. A method according to claim 10, wherein said reducing results in alteration of a phenotypic trait.

12. A method according to claim 10, wherein said indigenous RNA is messenger RNA.

13. A method according to claim 10, wherein said construct further comprises at least the right T-DNA border.

14. A method according to claim 10, wherein said transformed plant cell is grown into differentiated plant tissue.

15. A method according to claim 10, wherein said promoter provides for regulated expression.

16. A method according to claim 10, wherein the amount of RNA transcribed from said complementary strand present in said cell is less than the amount of said RNA indigenous to said cell.

17. A method according to claim 10, further comprising the step of recovering seed from a plant resulting from a cross between a first plant grown from said transformed plant cell and a second plant.

* * * * *

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
        ( A ) LENGTH: 219 base pairs
        ( B ) TYPE: nucleic acid
        ( C ) STRANDEDNESS: double
        ( D ) TOPOLOGY: linear (ii) MOLECULE TYPE: cDNA to mRNA (xi) SEQUENCE DESCRIPTION: SEQ ID NO: 1:

```
GAATTCCAT GGG ATT AAA GTG ATT AAT GTA CTT AGC TTT GGA GCT AAG GGT      51
          Gly Ile Lys Val Ile Asn Val Leu Ser Phe Gly Ala Lys Gly
           1           5                       10

GAT GGA AAA ACA TAT GAT AAT ATT GCA TTT GAG CAA GCA TGG AAT GAA        99
Asp Gly Lys Thr Tyr Asp Asn Ile Ala Phe Glu Gln Ala Trp Asn Glu
 15              20                  25                  30

GCA TGT TCA TCT AGA ACA CCT GTT CAA TTT GTG GTT CCT AAA AAC AAG       147
Ala Cys Ser Ser Arg Thr Pro Val Gln Phe Val Val Pro Lys Asn Lys
                 35              40                      45

AAT TAT CTT CTC AAG CAA ATC ACC TTT TCA GGT CCA TGC AGA TCT TCT       195
Asn Tyr Leu Leu Lys Gln Ile Thr Phe Ser Gly Pro Cys Arg Ser Ser
             50                  55                  60

ATT TCA GTA AAG ATT TTT GGA TCC                                       219
Ile Ser Val Lys Ile Phe Gly Ser
         65                  70
```